US00PP13028P2

(12) United States Plant Patent
Gradziel et al.

(10) Patent No.: US PP13,028 P2
(45) Date of Patent: Oct. 1, 2002

(54) CLINGSTONE PEACH TREE NAMED 'LILLELAND'

(75) Inventors: Thomas M. Gradziel; Mary Ann Thorpe, both of Davis; James A. Beutel, Winters; Robert E. Fenton, deceased, late of Port Hueneme, by Susan D. Fenton, legal representative; Vilmos Beres, deceased, late of Guernesville, by Marta M. Beres, legal representative; Clayton F. Weeks, Davis, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/891,286

(22) Filed: Jun. 27, 2001

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—Anne Marie Grünberg
(74) *Attorney, Agent, or Firm*—Burns, Doane, Swecker & Mathis, LLP

(57) ABSTRACT

A new and distinct cultivar of late-season clingstone peach tree (i.e., *Prunus persica*) is provided. Attractive, nearly symmetrical fruit is formed that is well suited for processing having uniform bright yellow flesh that is free from red staining at the pit cavity. The fruit ripens at approximately the same time as that of the 'Halford' cultivar (non-patented in the United States). The fruit color, flavor, and texture are believed to be superior to the 'Halford' cultivar. The flowers are large and showy and the growth habit is spreading to upright-spreading.

2 Drawing Sheets

BACKGROUND OF THE INVENTION

The new clingstone peach cultivar was created at Davis, Calif., U.S.A. during a breeding program of the University of California for the development of improved processing peaches. An objective of the program was to develop a superior replacement cultivar for the late-season 'Halford' cultivar (non-patented in the United States) that was introduced in 1921. This popular cultivar is heavily planted and is recognized to produce late-maturing fruit. The fruit flesh has a desirable yellow-gold color but often bears pink to red coloration near the pit cavity that is attributable to the formation of anthocyanins. This red coloration often oxidizes to brown when canned and thereby provides a less than optimum fruit color as well as an undesirable brown staining of the canned syrup. Additionally, the red-stained fruit stone or endocarp of the 'Halford' cultivar tends to be prone to breakage during processing and sometimes imparts unwanted pit fragments to the fruit flesh that are difficult to remove.

During the course of the breeding program that yielded the new cultivar of the present invention, many seedlings were developed and evaluated. The seed that produced the new cultivar of the present invention was produced by the open-pollination of University of California breeding line 'R, 13-33' (non-patented in the United States). A total of twenty seedlings from such open-pollination were planted in 1986. The new cultivar of the present invention was selected from among these seedlings and was initially designated 'F10EN, 6-27'. The evaluation and selection of the new cultivar of the present invention has continued over a number of years.

It was found that the new clingstone peach tree cultivar of the present invention:

(a) Exhibits a spreading to upright-spreading growth habit, (b) Forms large showy flowers, (c) Forms attractive nearly symmetrical fruit having uniform bright yellow flesh that is free from red staining at the pit cavity, (d) Ripens at substantially the same time as the 'Halford' cultivar (non-patented in the United States), and (e) Is patricularly well suited for processing.

The new cultivar has been asexually propagated at Davis, Calif., U.S.A., by grafting on peach rootstocks. Such propagation has confirmed that the characteristics of the new cultivar are stable and are reliably transmitted to subsequent generations.

The new cultivar of the present invention is considered to offer superior characteristics when compared to the popular 'Halford' cultivar and can be readily distinguished from such previously available cultivar. Unlike the 'Halford' cultivar, the fruit of the new cultivar is firmer and is free from red staining at the pit cavity. The fruit is of similar size and ripens at approximately the same late season as the 'Halford' cultivar. Also, the tree vigor is similar to that of the 'Halford' cultivar. The pit of the new cultivar tends to be smaller than that of the 'Halford' cultivar and thereby facilitates a greater processing case yield. Also, a lower frequency of pit fragments in the processed fruit flesh has been noted during observations to date. The level of soluble solids is similar to that of the 'Halford' cultivar. The fruit skin is less pubescent than that of the 'Halford' cultivar and tends to display a more uniform yellow-gold coloration. The leaves of the new cultivar are medium-sized with reniform glands and are a lighter green than those of the 'Halford' cultivar.

The new cultivar of the present invention has been tested in plantings at Davis, Calif.; Winters, Calif.; and Parlier, Calif., U.S.A.

Wood of the new cultivar has been subjected to the virus indexing program of Foundation Plant Materials Service, University of California at Davis, Calif., U.S.A. All indices have proven to be negative for viruses for foundation trees of this genotype being maintained by such Foundation Plant Materials Service.

The new cultivar of the present invention has been named 'Lilleland'.

DETAILED DESCRIPTION OF THE PHOTOGRAPHS

The accompanying photographs show typical specimens of trees, foliage, fruit, and stone of the new cultivar of the present invention in color as true as it is reasonably possible to make the same in color illustrations of this character. Trees of the new cultivar were being grown at Davis, Calif., U.S.A.

DETAILED DESCRIPTION

Figure 1:
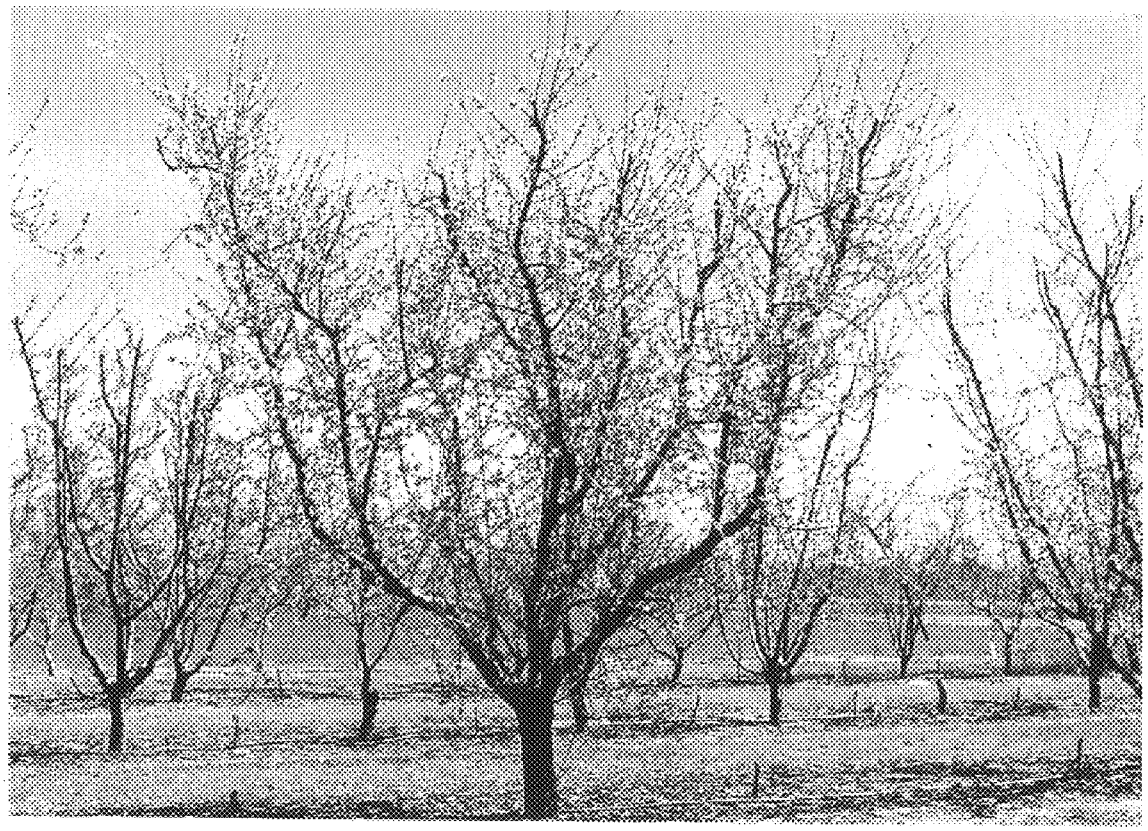
FIG. 1 illustrates trees having an age of approximately six years on Mar. 10, 2000. The large showy flowers are shown as well as the spreading to upright-spreading growth habit.
Figure 2:
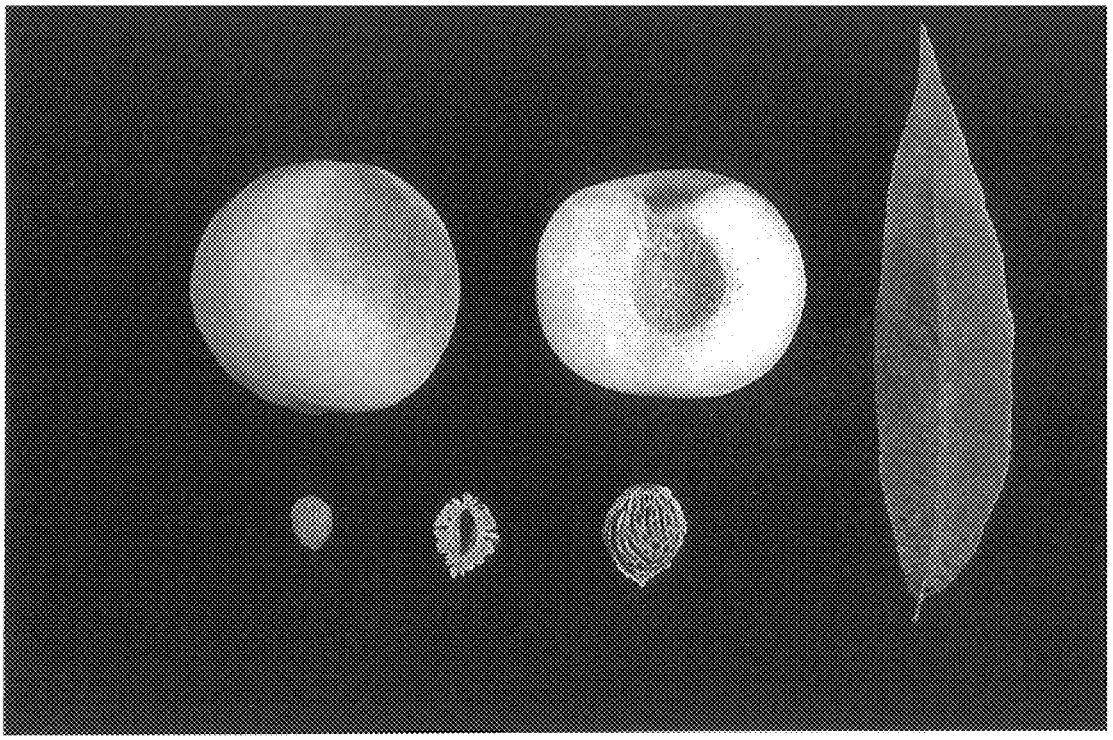
FIG. 2 illustrates on Aug. 11, 1999 external and internal views of the fruit, stone, and of a leaflet of the new cultivar.

The following is a detailed description of the new cultivar obtained from the observation of vegetatively propagated progeny of the new cultivar during the 1999 and 2000 growing seasons. The trees were grown at the Wolfskill Experimental Orchards of the University of California located at Winters, Calif., U.S.A., and at the University of California Pomology Research Plots located at Davis, Calif., U.S.A. The description is based on trees grown on standard peach rootstock 'Lovell' (unpatented). Color designations are presented with reference to the "Dictionary of Color" by Maerz and Paul, First Edition (1930). More common color terms are to be accorded their customary dictionary significance.

Botanical classification: *Prunus persica*, cv. 'Lilleland'.

Tree:

*Size.*—Medium. The trees resulting from the asexual propagation of 1998 during the fall of 2000 had a height of approximately 3.4 meters, a breadth of approximately 3.5 meters across the crown, and commonly possessed approximately four scaffolds.

*Vigor.*—Medium. Produced approximately 0.62 to 0.88 meter of new growth during the 2000 growing season.

*Growth.*—Spreading to upright-spreading.

*Hardiness.*—Hardy under typical Sacramento Valley climatic conditions.

*Production.*—Productive.

*Bearing.*—Regular bearer.

Trunk:

*Size.*—Medium to large. The trunk diameter at 10 cm above the ground is approximately 22 to 24 cm. The scaffold diameters at the base of the scaffolds are approximately 12 cm.

*Texture.*—Relatively coarse with substantial scarfskin.

*Color.*—The bark color ranges from brown-grey (15-C-4 Pelt Brown) to more medium brown (8-J-9 Hindu Brown).

*Lenticels.*—Numerous, large, flattened and generally oval-shaped. Typically the lenticels range from approximately 2 to 7 mm in width at a right angle to the trunk and are approximately 1 to 3 mm in height. The lenticel surface is light brown in coloration (13-J-10) and is somewhat calloused.

Branches:

*Size.*—Medium.

*Texture.*—Medium.

*Color.*—Mature shoots are light brown (14-G-9) to darker brown (15-E-10 Olive Wood). The current season's shoots are pale light green (18-K-6). The esposed surfaces are commonly tinged rose-red (6-K-11 Cauldron). The coloration of the new expanding shoot tips is bright yellow green (17-L-4).

*Lenticels.*—Somewhat linear at a right angle to the shoots, and light in coloration.

*Internode length.*—On current season's hanger shoots the length between nodes commonly is approximately 12 to 28 mm.

Leaves:

*Size.*—Medium to large. Typical length from vigorous current season's growth is approximately 15.5 to 17.8 cm including the petiole, and typical width is approximately 3.5 to 4.5 cm. The leaf thickness is average.

*Form.*—Lanceolate.

*Apex.*—Acuminate and often curves downward.

*Aspect.*—The blade commonly ranges from substantially flat to somewhat folded upwards.

*Color.*—The upper surface is dark green (23-J-6 Cyprus Green) and the lower surface is a much lighter grey-green (21-I-6). The primary and mid-vein on the under surface is pale yellow-green (17-I-2).

*Margin.*—Crenate and occasionally double crenate. The crenations are relatively large and uniform. The leaf margins commonly range from straight to moderately undulate.

*Petiole.*—Generally medium in size, commonly approximately 8 to 11.4 mm in length, approximately 2 mm in thickness, and pale yellow-green in coloration (17-K-5).

*Glands.*—Small to medium in size, almost always reniform, alternate, commonly 1 to 2 on the petiole, often borne on a short stalk, and frequently 0 to 2 additional glands can be observed at the base of the leaf blade. The coloration is shiny light green-yellow (17-K-5) and often with a reddish center.

*Stipules.*—Linear lanceolate in configuration, most are early deciduous, margins are serrate, commonly approximately 6 to 9 mm in length, and the coloration of young stipules commonly is light green-yellow (17-K-5) with darkening to brownish upon aging.

Fruit:

*Maturity when described.*—Full commercial maturity.

*Picking.*—First pick was Aug. 26, 2000 and last pick was Aug. 30, 2000.

*Season of maturity.*—Approximately concurrent with or one day later than the 'Halford' cultivar.

*Size.*—Uniform, large. Average axial diameter is approximately 59 to 64 mm, the average suture diameter is approximately 62 to 70 mm, and the average cheek diameter is approximately 61 to 68 mm.

*Form.*—Globose to slightly oblate in lateral aspect, and in the apical aspect is nearly globose with slight variability.

*Suture.*—As an inconspicuous line. Is slightly deeper at the base and at the apex.

*Ventral surface.*—Rounded and slightly lipped at the base.

*Base.*—Rounded. The base angle commonly is variable from a substantially right angle to oblique.

*Stem cavity.*—Broad and moderately deep, commonly approximately 3.4 cm in length on average, approximately 2.5 cm in width on average, and approximately 1.7 cm in depth on average.

*Apex.*—Commonly rounded with a low tip. A slight depression commonly is present on the ventral surface next to the apex.

*Pistil point.*—Most frequently is oblique.

*Stem length.*—Medium, and commonly averages 1.2 cm.

*Stem thickness.*—Commonly averages approximately 3 to 3.5 mm and usually is more thickened at the distal end.

*Skin pubescence.*—Fine, short, and matted. Commonly with less pubescence than the 'Halford' cultivar.

*Skin tendency to split.*—None observed.

*Skin color.*—The primary ground color is uniform orange-yellow (10-J-5). The fruit surface has a moderate amount of blush coloration that commonly covers approximately 20 to 50 percent of the total surface. Fruit exposed to direct sunlight commonly possesses more blush. The blush pattern is primarily washed with a moderate amount of dark mottling. The blush color ranges from dark garnet red (7-J-6) to a lighter shade of red (6-L-7) with a range of variation in between.

*Flesh color.*—A uniform yellow coloration from the skin to the stone cavity (10-K-4).

*Flesh texture.*—Firm, and non-melting.

*Flesh fibers.*—Few in number, short and fine.

*Ripening.*—Ripens evenly.

*Flavor.*—High quality.

*Aroma.*—Pleasant and moderate.

*Eating quality.*—Good.

*Canning quality.*—Very good.

*Stone type.*—Clingstone with flesh connected over the entire stone surface.

*Stone size.*—Small to medium and commonly averages approximately 31.2 mm in length, approximately 21.4 mm in width, and approximately 17.6 mm in thickness.

*Stone fibers.*—Numerous very short and fine fibers attached laterally to the stone.

*Stone form.*—Variable, but most often slightly obovate.

*Stone base.*—Moderately narrow and medium truncate in form. The base angle is variable, most often is slightly oblique to the stone axis, and is shorter on the ventral surface side.

*Stone hilum.*—Medium in size, well defined, and oval.

*Stone apex.*—Generally rounded with a broad rather blunt tip.

*Stone sides.*—Variable and most often nearly equal.

*Stone surface.*—Moderately coarse with the heaviest grooving being present near the ventral suture running nearly parallel to the suture.

*Ventral edge.*—Medium in width with several low wings. Such wings are the most prominent from mid-suture to the stone base.

*Dorsal edge.*—Somewhat variable in form, and most commonly the dorsal suture is moderately narrow. The apical shoulder area is substantially eroded and substantially concave in configuration.

*Stone color.*—When dry, hazel-brown (13-D-8).

*Tendency to split.*—None observed.

Flowers:

*Chilling season.*—Low to medium for the growing location. There were approximately 1,200 chilling hours below 45° F. for the 1999 winter season, and approximately 770 hours below 45° F. for the 2000 winter season.

*Buds.*—Medium to large in size, conic in form, plump, free of the stem with moderately pubescent surfaces of light grey coloration. The exterior bud scale ranges from grey (15-A-6 Beaver Grey) to grey-brown (15-A-8 Winter Leaf Brown) in coloration. The buds are hardy under typical climatic conditions of the Sacramento Valley. There commonly are one to two floral buds per node.

*Bloom timing.*—Mid- to late-season in relation to other commercial cling peach cultivars. During 1999 and 2000 the bloom periods were substantially the same as the 'Halford' cultivar.

*Size.*—The flower size is large and showy. The fully expanded flower diameter commonly is approximately 30 to 45 mm.

*Bloom quality.*—Commonly abundant throughout the tree. There commonly are two flowers per node.

*Petals.*—The petal size is large and commonly ranges from approximately 18 to 22 mm in length and from approximately 17 to 22 mm in width. The petal number is five. The petal form is broadly ovate. The young petals are light pink (1-C-3) and darken slightly at maturity to (1-D-3). The petal claw is moderately large and truncate in form. The claw color is dark rose-pink (1-I-4 Casino Pink) and darker than the overall petal. The petal margins are somewhat ruffled. The petal apices are variable, most frequently rounded and are somewhat raised at times.

*Pedicel.*—Quite short and commonly exhibits a length of approximately 1 to 1.5 mm and a thickness of approximately 1 to 1.5 mm. The coloration is bright green (17-L-6) and the surface is glabrous.

*Nectaries.*—Bright orange (9-C-11) and become slightly darker at maturity.

*Calyx.*—Glabrous and quite rugose, and the coloration is light maroon (5-J-4) with areas of green (19-L-2 Jewel Green) especially basally, and darkening to intense maroon (6-J-5 Rubaiyat). The lobes are approximately 6 mm in length and approximately 4 mm in width.

*Sepals.*—Moderately pubescent with greyish pubescence, average in size, conic in form, and dark maroon (6-K-4 to 6-J-5) in coloration.

*Anthers.*—Average in size, dark red dorsally (5-L-11 Brickdust) and tan-red ventrally (4-A-10 Woodland Rose).

*Stamens.*—Variable in length and commonly range from approximately 12 to 18 mm in length. Frequently extend above the pistil. The filaments are very pale pink when young (1-C-1) and become dark maroon (3-J-5) with advancing maturity. The number commonly averages approximately 25 to 30.

*Pollen.*—Abundant yellow-gold (10-K-5) in coloration.

*Pistil.*—Pubescent basally over the ovary, and less so near the stigma and over the upper style area. The length commonly is approximately 12 to 15 mm including the ovary. The coloration basally is pale green (17-J-3) and a paler green (17-J-1) over the upper style area.

Major use: Canning.
Keeping quality: Good.
Resistance to insects and diseases: Average.

We claim:

1. A new and distinct cultivar of clingstone peach tree having the following combination of characteristics:

(a) Exhibits a spreading to upright-spreading growth habit, (b) Forms large showy flowers, (c) Forms attractive nearly symmetrical fruit having uniform bright yellow flesh that is free from red staining at the pit cavity, (d) Ripens at substantially the same time as the 'Halford' cultivar (non-patented in the United States), and (e) Is particularly well suited for processing;

substantially as illustrated and described.

* * * * *